US012004809B2

United States Patent
Rochon

(10) Patent No.: US 12,004,809 B2
(45) Date of Patent: Jun. 11, 2024

(54) ENDOVENOUS TREATMENT ASSEMBLY AND DEVICE

(71) Applicant: LSO MEDICAL, Loos (FR)

(72) Inventor: Philippe Rochon, Loos (FR)

(73) Assignee: LSO MEDICAL, Loos (FR)

( * ) Notice: Subject to any disclaimer, the term of this patent is extended or adjusted under 35 U.S.C. 154(b) by 203 days.

(21) Appl. No.: 16/763,699

(22) PCT Filed: Nov. 12, 2018

(86) PCT No.: PCT/EP2018/080857
§ 371 (c)(1),
(2) Date: May 13, 2020

(87) PCT Pub. No.: WO2019/092228
PCT Pub. Date: May 16, 2019

(65) Prior Publication Data
US 2020/0367968 A1    Nov. 26, 2020

(30) Foreign Application Priority Data
Nov. 13, 2017 (FR) ..................... 1760627

(51) Int. Cl.
*A61B 18/24* (2006.01)
*A61B 17/00* (2006.01)
*A61B 18/22* (2006.01)

(52) U.S. Cl.
CPC .... *A61B 18/24* (2013.01); *A61B 2017/00469* (2013.01); *A61B 2018/225* (2013.01)

(58) Field of Classification Search
CPC .......... A61M 16/0497; A61M 16/0875; A61M 2205/02; A61M 2209/06;
(Continued)

(56) References Cited

U.S. PATENT DOCUMENTS 4,114,626 A * 9/1978 Beran ............... A61M 16/0488
248/74.1
6,102,905 A * 8/2000 Baxter ..................... A61L 2/10
606/7
(Continued)

FOREIGN PATENT DOCUMENTS

EP    2489394 A1    8/2012
JP    2001517508 A    10/2001
(Continued)

OTHER PUBLICATIONS

Int'l. Search Report for corresponding Russian Patent Appln. No. 2020114707, dated Feb. 14, 2022.
(Continued)

*Primary Examiner* — Yingchuan Zhang
*Assistant Examiner* — Sebastian X Lukjan
(74) *Attorney, Agent, or Firm* — David D. Brush; Westman, Champlin & Koehler, P.A.

(57) ABSTRACT

An endovenous treatment assembly includes a wire element for delivering treatment doses, which is flexible and capable of being inserted, over a portion of its length, longitudinally into a vein, and a positioning and guiding part that manipulates the wire element. The positioning and guiding part includes at least a first means for guiding in translation a first portion of the wire element, the wire element being able to slide in the direction of its length relative to the first guiding means. The positioning and guiding part further includes a first mechanical assembly for removable mounting relative to a drive system, so that the first portion of the wire element can be positioned and guided by the positioning and guiding part so as to be able to be engaged with of the drive system for driving the wire element in the direction of its length at least in a first direction.

26 Claims, 13 Drawing Sheets

(58) Field of Classification Search
CPC ........ A61M 2209/088; A61M 2209/08; A61M 2209/082; A61M 2209/084; A61M 5/1418; B62B 1/12; B62B 2204/00; B62B 2501/065; F16L 3/13; F16L 3/223; A61B 18/24; A61B 2017/00469; A61B 2018/225; A61B 18/22

See application file for complete search history.

(56) References Cited

U.S. PATENT DOCUMENTS

| | | | |
|---|---|---|---|
| 6,485,482 | B1 | 11/2002 | Belef |
| 6,814,727 | B2 | 11/2004 | Mansouri-Ruiz |
| 8,870,815 | B2 | 10/2014 | Bhat et al. |
| 9,101,269 | B2 | 8/2015 | Selkee |
| 2005/0131400 | A1 | 6/2005 | Hennings et al. |
| 2005/0203496 | A1* | 9/2005 | Ritchie .................. A61B 18/24 606/15 |
| 2005/0203497 | A1* | 9/2005 | Speeg .................... A61B 18/24 606/15 |
| 2005/0222554 | A1 | 10/2005 | Wallace et al. |
| 2008/0097224 | A1 | 4/2008 | Murphy et al. |
| 2008/0097227 | A1 | 4/2008 | Zdeblick et al. |
| 2008/0097408 | A1 | 4/2008 | Murphy et al. |
| 2010/0069833 | A1 | 3/2010 | Wenderow et al. |
| 2012/0203168 | A1 | 8/2012 | Fujimoto et al. |
| 2014/0074153 | A1 | 3/2014 | Fujimoto et al. |
| 2015/0012008 | A1 | 1/2015 | Mcweeney |
| 2015/0113736 | A1 | 4/2015 | Cox et al. |
| 2015/0342679 | A1* | 12/2015 | Boutoussov ........... A61B 18/20 606/16 |

FOREIGN PATENT DOCUMENTS

| | | | |
|---|---|---|---|
| RU | 2555381 C2 | 7/2015 | |
| RU | 2608440 C2 | 1/2017 | |
| WO | 99/15237 A1 | 4/1999 | |
| WO | 9915237 A1 | 4/1999 | |
| WO | WO-9915237 A1 * | 4/1999 | ............. A61B 18/24 |
| WO | 2011046028 A1 | 4/2011 | |

OTHER PUBLICATIONS

Int'l. Search Report for PCT/EP2018/080857, dated Jan. 23, 2019.
English translation of the Written Opinion of the International Searching Authority dated Jan. 23, 2019 for corresponding International Application No. PCT/EP2018/080857, filed Nov. 12, 2018.
Japanese Notice of Reason for Rejection dated Jan. 6, 2023 for corresponding Japanese Application No. 2020-544145.
Chinese Office Action dated Apr. 26, 2023 for corresponding Chinese Application No. 201880079932.6.

* cited by examiner

ENDOVENOUS TREATMENT ASSEMBLY AND DEVICE

TECHNICAL FIELD

The present invention relates to the field of endovenous treatment by delivery into the vein of a treatment dose by means of a flexible wire element. The treatment dose may, in a non-limiting and non-exhaustive manner, consist of a dose of energy, delivered for example in the form of electromagnetic radiation, by means of sound or ultrasonic waves, radio-frequency waves, or a dose of thermal energy delivered by radiation and/or contact, or a dose of a product allowing treatment of the vein. The flexible wire element may be hollow or solid, and may in particular, in a non-limiting and non-exhaustive manner, be an optical fiber, a cable-type wire element or a flexible probe or a flexible cannula.

PRIOR ART

In the field of endovenous treatment, the treatment of a vein via delivery into the vein of treatment doses by means of a flexible wire element, which is inserted longitudinally into the vein, and whose withdrawal must be controlled during treatment, constitutes prior knowledge. More particularly, in the field of endovenous laser therapy, better known by the acronym EVLT, it is customary to treat a vein by means of an endovenous laser (for example for the occlusion of saphenous varices by endovenous laser), the flexible wire element of which is an optical fiber used to emit electromagnetic radiation into the vein. For other types of endovenous treatment, the flexible wire element may, in a non-limiting and non-exhaustive manner, also be a flexible cable or probe or a flexible cannula.

Examples of endovenous treatment apparatus are described, for instance, in the following publications: US 2005/0131400, US2008/0097224, US2008/0097408, U.S. Pat. No. 6,814,727.

Usually, the removal of the flexible wire member inserted longitudinally into the vein, for example an optical fiber, can be controlled during treatment by the practitioner by means of a motorized drive system, still called a pulling system, to pull longitudinally on the end portion (farthest from the patient's body) of the flexible wire element by controlling the withdrawal speed. Such withdrawal can be carried out continuously or step by step. Motorized withdrawal systems commonly used include drive means in the form of at least one pair of drive rollers (or rollers) between which the flexible wire element passes and which allow the drive of this wire element by friction.

The implementation of a drive system in which the flexible wire element can be driven by friction or the like, by being engaged with drive means, such as for example (but not exclusively) rollers or drive rollers, for its drive by said drive means in the direction of its length at least in a first direction, and preferably also in the reverse direction, has the advantage of allowing movement of the flexible wire element over a very large stroke, and in particular over a stroke which can possibly reach almost the entire length of this flexible wire element.

Flexible wire dose delivery devices, such as an optical fiber, are usually single-use consumables that are discarded after they have been used.

In practice, at each treatment the practitioner removes from his sterile packaging the flexible wire element for delivering doses, such as for example an optical fiber and must correctly position by hand a portion of this flexible wire element between the drive rollers of the drive system.

These operations of handling and positioning of the flexible wire element for delivering doses with respect to the drive rollers of the drive system are restrictive and tedious for the practitioner and can also cause accidental deterioration of the wire element flexible delivery of doses, in particular when it is an optical fiber. In addition, it may happen that the practitioner does not correctly position on his first attempt the flexible wire element of delivery of doses relative to the drive rollers of the drive system and that they have to start again several times.

Moreover, it is advantageous to be able to operate a wire element having a significant length, so as to easily be able to locate the motorized withdrawal system and the treatment dose-delivery system outside the sterile operating field, such as, for example, the laser source in the case of an endovenous laser. However, this great length of the wire element poses a problem of space requirement, particularly during the operations of removal of the wire element.

In the international patent application WO99/15237, a technical solution has also already been proposed using a part for positioning and guiding an optical fiber with respect to a drive system for the optical fiber. In this solution, the optical fiber is not driven by friction, but is attached to a piston which is mounted inside a positioning and guiding part. The positioning and guiding part is adapted to be removably attached to a drive system having a translationally movable rod, so that said rod can push on the piston, thus causing the displacement of the optical fiber attached to the piston, lengthwise in a first direction. A return spring is also mounted in the positioning and guiding part and allows a return to the piston position and therefore a displacement of the optical fiber attached to the piston in the opposite direction.

This solution described in international patent application WO99/15237 cannot be used with a drive system in which the wire element for delivering treatment doses can be driven by friction or the like, by being engaged with drive means, such as for example (but not exclusively) rollers or drive rollers, for its drive by said drive means in the direction of its length at least in a first direction, and preferably also in the reverse direction.

In addition, disadvantageously, in the solution described in international patent application WO99/15237, the stroke of the displacement of the wire element for delivering treatment doses is very small and is limited to the stroke of the drive piston.

Purpose of the Invention

An objective of the invention is generally to propose in the field of endovenous treatment a new technical solution which makes it possible to simplify and make reliable the operations of manipulation and positioning of the flexible wire element for delivering treatment doses with respect to drive means of the drive system of an endovenous device.

A more specific optional objective is to propose a new technical solution which does not have the above-mentioned drawback of limiting the displacement stroke of the wire element for delivering treatment doses, inherent in the solution described in the international patent application WO99/15237.

SUMMARY OF THE INVENTION

The subject of the invention is therefore an endovenous treatment assembly comprising a wire element for delivering treatment doses, which is flexible and capable of being inserted, over part of its length, longitudinally into a vein, and a positioning and guiding part, which is integral with the wire element for delivering treatment doses so as to allow the manipulation of the wire element for delivering treatment doses by means of this positioning and guiding part; said positioning and guiding part comprises at least a first guiding means for guiding in translation a first portion of the wire element for delivering treatment doses in the direction of its length, the wire element for delivering treatment doses being able to slide in the direction of its length relative to said first guiding means of said positioning and guiding part and said positioning and guiding part comprising first mechanical assembly means allowing its removable mounting relative to a drive system, so that said first portion of the wire element for delivering treatment doses can be positioned and guided by means of this positioning and guiding part while being engaged with drive means of the drive system for driving the wire element for delivering treatment doses in the direction of its length at least in a first direction.

The invention also relates to an endovenous treatment assembly comprising a wire element for delivering treatment doses, which is flexible and capable of being inserted, over part of its length, longitudinally into a vein, and a positioning and guiding part, which is integral with the wire element for delivering treatment doses so as to allow the manipulation of the wire element for delivering treatment doses by means of this positioning and guiding part; the wire element for delivering treatment doses can slide in the direction of its length relative to said positioning and guiding part; said positioning and guiding part comprises at least a first means for guiding in translation a first portion of the wire element for delivering treatment doses in the direction of its length and first mechanical assembly means allowing its removable mounting with respect to a drive system comprising at least one pair of drive rollers, so that said first portion of the wire element for delivering treatment doses can be positioned and guided by means of this positioning and guiding part between the drive rollers, for driving the wire element for delivering treatment doses in the direction of its length at least in a first direction.

More specifically, the invention assembly may include the following additional and optional features, taken in isolation, or in combination with each other:

said first portion of the wire element for delivering treatment doses is accessible or can be made accessible.

said first portion of the wire element for delivering treatment doses can be positioned and guided by means of the positioning and guiding part so as to be able to be engaged with drive means of the drive system for driving of the wire element for delivering treatment doses in the direction of its length at least in a first direction, with a displacement of the wire element for delivering treatment doses in the direction of its length relative to said means for training.

the first mechanical assembly means allow rapid and tool-free assembly of the positioning and guiding part.

the assembly includes second means for guiding a second portion of the wire element for delivering treatment doses.

the second guide means guide in translation this second portion of the wire element for delivering treatment doses by making it perform at least a quarter turn and preferably at least a half turn.

the second guide means are an integral part of the positioning and guiding part.

the wire element for delivering treatment doses has a third portion, which extends to the rear end of the wire element for delivering treatment doses, and which is not integral with the positioning and guiding part or which is integral with the positioning and guiding part but can be separated from this positioning and guiding part.

the assembly includes a coupler which is attached to the rear end of the wire element for delivering treatment doses and which allows the wire element for delivering treatment doses to be connected to a source of treatment doses.

the positioning and guiding part is a single part, and more particularly a molded part.

the positioning and guiding part is constituted by a monolithic assembly.

the assembly includes a flexible guide threaded on a front portion of the wire element for delivering treatment doses, said wire element for delivering treatment doses being able to slide longitudinally relative to the flexible guide.

the rear end of the flexible guide is integral with the positioning and guiding part, so as to axially block the rear part of the flexible guide at least in the first drive direction of the wire element for delivering treatment doses, and preferably also in the direction opposite to the direction of drive of the wire element for delivering treatment doses.

the assembly comprises a storage support, on which is wound all or part of the front portion of the wire element for delivering treatment doses which extends from the front end of the wire element for delivering doses up to said first portion of the wire element for delivering treatment doses.

the flexible guide and the part of the wire element for delivering treatment doses threaded into the flexible guide are wound on the storage support.

the storage support and the positioning and guiding part are separated or the storage support and the positioning and guiding part are assembled and separable from each other.

the wired treatment dose delivery element is an optical fiber.

The assembly also includes a holding system which makes it possible to temporarily hold the front end portion of the flexible guide relative to the body of a patient, near the insertion area of the wire element for delivering treatment doses.

the holding system includes a holding part which is fastened or can be fastened to the front end portion of the flexible guide and which is designed to be applied to the body of a patient so as to temporarily hold the extreme front end portion of the flexible guide relative to the body of a patient, close to the insertion zone of the wired treatment dose delivery element.

the holding system comprises fixing means which make it possible to temporarily fix the holding part applied to the body of a patient near the insertion point of the wire element for delivering treatment doses, and preferably which comprise an adhesive suitable for being bonded to the skin.

the positioning and guiding part, the wire element for delivering treatment doses, where appropriate the flexible guide, and where appropriate the storage support, are sterile and placed in an airtight package.

The invention also relates to an endovenous treatment device comprising one or other of the aforementioned assemblies and a drive system, preferably motorized, which comprises drive means, the device further comprising second mechanical assembly means adapted to cooperate with the first mechanical assembly means of the positioning and guiding part, so as to allow said removable mounting of the positioning and guiding part with respect to the drive system, so that said first portion of the wire element for delivering treatment doses is positioned so as to be able to be engaged with drive means of the drive system and the drive means of the drive system allow the drive of the wire element for delivering treatment doses in the direction of its length at least in a first direction, with preferably a displacement of the wire element for delivering treatment doses in the direction of its length relative to said drive means.

More specifically, the device constituting the invention may include the following additional and optional features, taken in isolation, or in combination with each other:

- the second mechanical assembly means are integral with or form an integral part of the drive system.
- the drive means of the drive system comprise at least one pair of drive rollers and the second mechanical assembly means are adapted to cooperate with the first mechanical assembly means of the positioning and guiding part, so to allow the positioning of the first portion of the wire element for delivering treatment doses between the drive rollers.
- the drive means of the drive system allow friction drive of the wire element (1) for delivering treatment doses.
- the endovenous treatment device further comprises a source of treatment doses capable of being connected to the rear end of the wire element for delivering treatment doses.
- the drive system and the source of treatment doses are an integral part of the same monolithic unit.
- the wire element for delivering treatment doses is an optical fiber and the source for treatment doses is a source of electromagnetic radiation.

The invention also relates to a use of the aforementioned endovenous treatment device for treating a vein, and in particular for treating a vein by means of electromagnetic radiation.

The subject of the invention is also a method for preparing an aforementioned endovenous treatment device or a method for endovenous treatment by means of the aforementioned endovenous treatment device, during which the positioning and guiding part is removably mounted with respect to the drive system, and preferably on the drive system, so that a first portion of the wire element for delivering treatment doses is positioned so as to be able to be engaged with the drive means of the drive system and can be driven at least in a first drive direction.

BRIEF DESCRIPTION OF THE DRAWINGS

The features and advantages of the invention will become apparent from reading the detailed description below of several particular embodiments of the invention, which particular embodiments are described as non-limiting and non-exhaustive examples of the invention, and with reference to the accompanying drawings in which.

DETAILED DESCRIPTION

Figure 1:
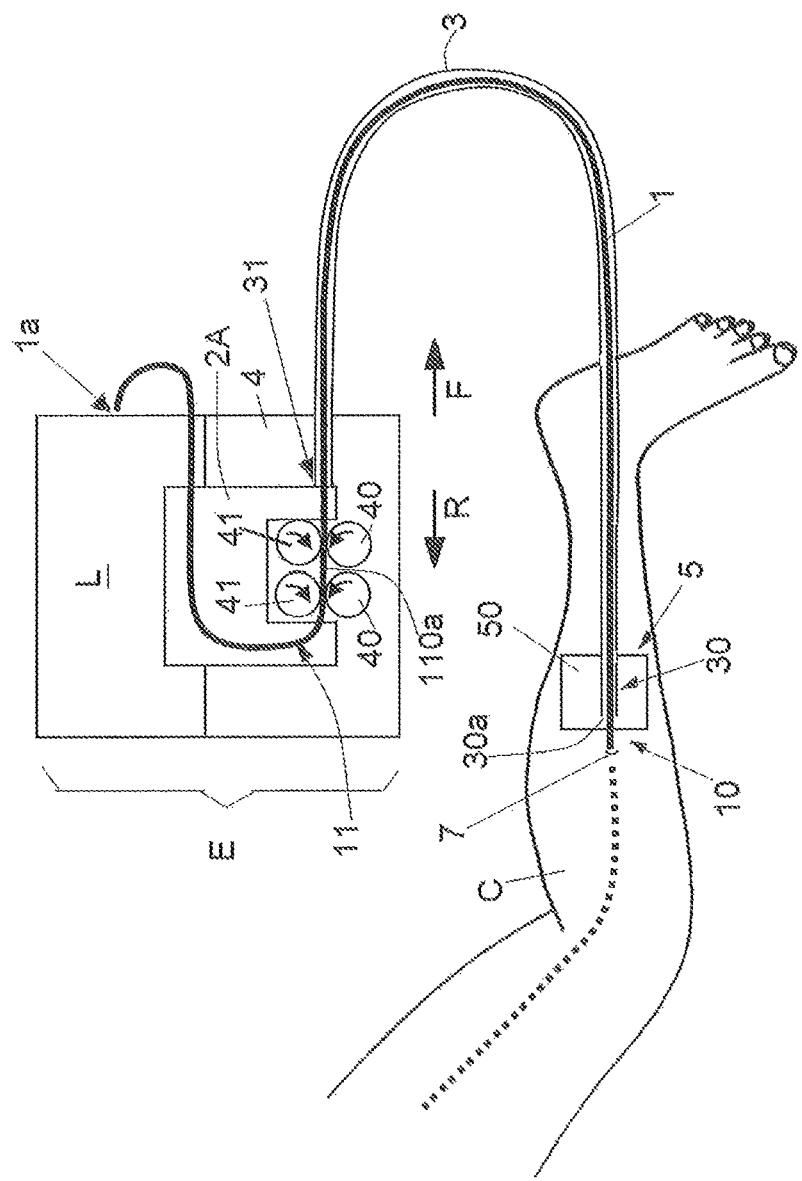
FIG. 1 is a schematic general view showing an example of an implementation of an endovenous treatment device relating to the invention, of the endovenous laser type, for laser treatment of a vein in the leg.

A schematic view of an endovenous treatment device with controlled withdrawal is shown in FIG. 1, according to the invention, in use for the treatment of a vein.

This endovenous treatment device with controlled withdrawal includes:

- a flexible wire element 1 for delivering treatment doses into the vein, which flexible wire element 1 is an optical fiber in the particular example described in detail below,
- a motorized drive system 4 which enables a pulling force to be exerted, in a controlled manner and towards the rear (direction R), upon the optical fiber 1,
- a positioning and guiding part 2A which will be described in detail below, and which allows rapid and reliable positioning and guiding in translation of the optical fiber 1 relative to the drive means of the motorized drive system 4,
- a source of electromagnetic radiation L, of the laser source type, which is coupled to the rear end 1a of the optical fiber 1,
- a flexible guide sheath 3, which surrounds and guides the optical fiber 1 over a front portion of its length, the optical fiber 1 being able to slide longitudinally relative to the sheath 3.

With reference to FIG. 1, the flexible guide sheath 3 has a rear end part 31 and, on the opposite side, a front end part 30, which ends with a front opening 30a allowing the passage of the optical fiber 1. The optical fiber 1 is threaded into the guide sheath 3, so that the guide sheath 3 surrounds and guides the optical fiber 1 over a portion of its length, with a rear end part 11 of the optical fiber 1, and opposite a front end part 10 of the optical fiber 1 positioned outside the guide sheath 3. The front end of the optical fiber 1 which allows the emission of electromagnetic radiation in the vein is thus positioned outside the guide sheath 3.

The rear end part 31 of the flexible sheath is integral with the positioning and guiding part 2A, so as to axially block this rear part 31 of the guide sheath 3, relative to the optical fiber 1, at least in the withdrawal direction R of the optical fiber 1, and preferably also in the opposite direction of advancement F of the optical fiber 1, the optical fiber 1 being able to slide longitudinally relative to the guide sheath 3. The motorized drive system 4 thus makes it possible to pull the optical fiber 1 backwards (arrow R) by sliding it relative to the sheath 3.

The sheath 3 allows sliding of the optical fiber 1 with preferably a minimum of friction and is preferably biocompatible. The inner diameter of the sheath 3 must also be adjusted relative to the outer diameter of the optical fiber 1, in order to limit the radial movement of the optical fiber 1 in the sheath 3 and to allow efficient transfer of the longitudinal movements. If the difference between the inside diameter of the sheath 3 and the outer diameter of the optical fiber 1 is too great, it can cause a detrimental divergence between the moment when the motor of the drive system 4 is activated and the moment of actual sliding of the fiber with respect to the sheath. By way of non-limiting and non-exhaustive examples, with an optical fiber 1 having an outside diameter of 900 μm, a sheath 3 having, for example, an internal diameter of 1000 μm, and with an optical fiber 1 having an outside diameter of 600 μm, a sheath 3 having for example an inner diameter of 700 μm is used.

Various materials can be used for the sheath 3, including, in a non-limiting and non-exhaustive manner, the following materials: silicone, polyurethane, PTFE, PET, ETFE, latex, thermoplastic elastomer.

In the particular embodiment in FIG. 1, but in a non-limiting manner for the invention, the device also features a holding system 5 which enables the front end part 30 of the guide sheath 3 to be attached temporarily to the body C of a patient (in this case in FIG. 1 and in a non-limiting manner on a leg) near the insertion point 7 of the optical fiber in the body C.

It should be noted that in the context of the invention, the flexible guide sheath 3 and/or the holding part 5 are optional and may not be implemented in another variant embodiment of the invention.

The drive system 4 comprises two pairs of rotary drive rollers 40, 41, between which a first straight portion 110a of the optical fiber 1 is positioned and guided by the part 2A. The rollers 40 are for example motorized driving rollers and the rollers 41 are for example rollers mounted free in rotation. These rotary drive rollers 40, 41 make it possible to frictionally drive the optical fiber 1 to the rear (direction R) at a controlled speed which depends on the rotation speed of the rollers 40, 41 during the controlled removal of the optical fiber from the vein to be treated. In this particular embodiment variant, when the optical fiber 1 is driven by friction by the rotary rollers 40, 41, it moves in the direction of its length relative to these rollers.

In another embodiment variant, the drive system 4 may comprise only a pair of rotary drive rollers 40, 41. More generally, the rotary drive rollers 40, 41 can be replaced by any equivalent means fulfilling the function of driving the optical fiber in the direction of its length with preferably a displacement of the optical fiber in the direction of its length with respect to said drive means. This driving of the optical fiber is not necessarily carried out by friction, but more generally by means of any drive means which can be engaged with the optical fiber. The drive means may for example comprise a clamp, which is movable in back-and-forth translation between two extreme positions, and which is controlled to grip the first accessible portion 110a of the optical fiber 1, during the translational movement of the clamp from a first extreme position to the other, and to let go and no longer be engaged with the optical fiber during the return movement of the clamp in the opposite direction. In the embodiment variant in FIG. 1, the drive system 4 for the controlled withdrawal of the optical fiber 1 and the electromagnetic radiation source L advantageously form an integral part of the same monolithic assembly E. In another embodiment variant, the drive system 4 can however be separated and distant from the electromagnetic radiation source L.

Figure 2:
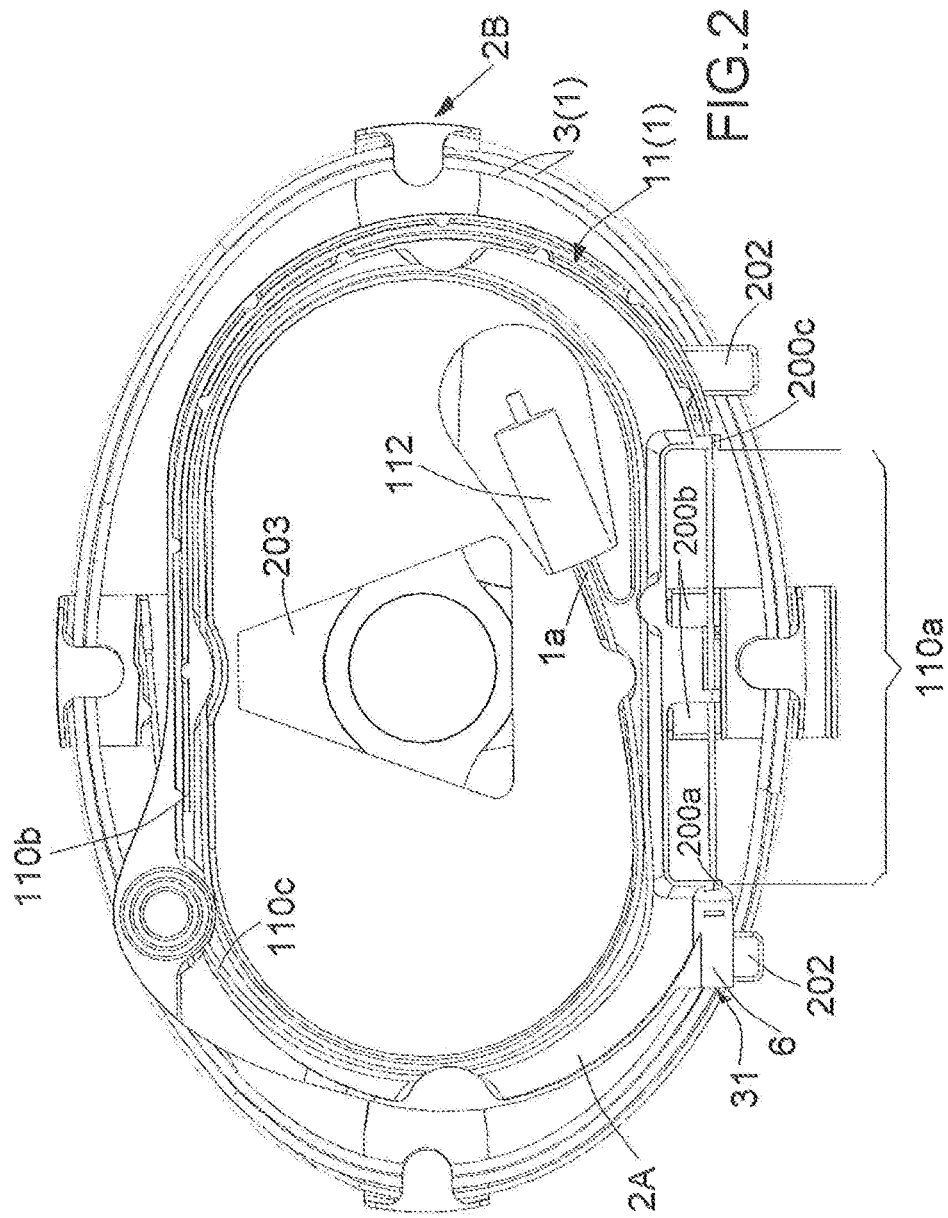
FIG. 2 is an isometric view of a particular variant of an endovenous treatment assembly of the invention, packaged in its transport and/or storage configuration.
Figure 3:
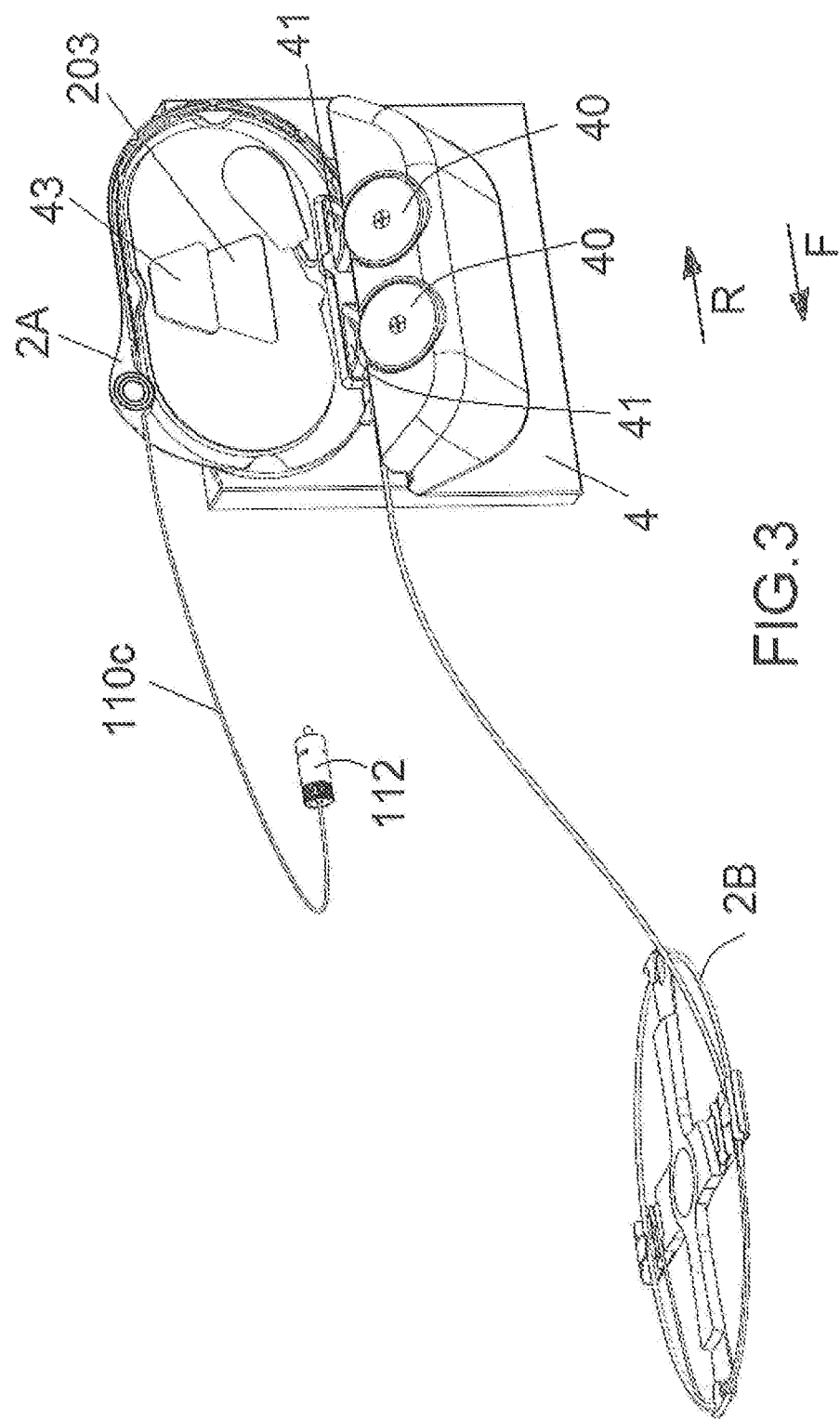
FIG. 3 is an isometric view of the assembly of FIG. 2, once the storage support separated from the positioning and guiding part, and the positioning and guiding part being mounted on a drive system.

With reference to FIGS. 2 and 3, in this particular embodiment, the endovenous device also includes a storage support 2B on which are wound all or part of the portion of the optical fiber 1 which extends from the front end of the optical fiber 1 to said first portion 110a of the optical fiber 1 and all or part of the flexible sheath 3 threaded on the optical fiber 1. This storage support 2B makes it possible to facilitate the transport, storage and handling of the optical fiber 1.

Figure 4:
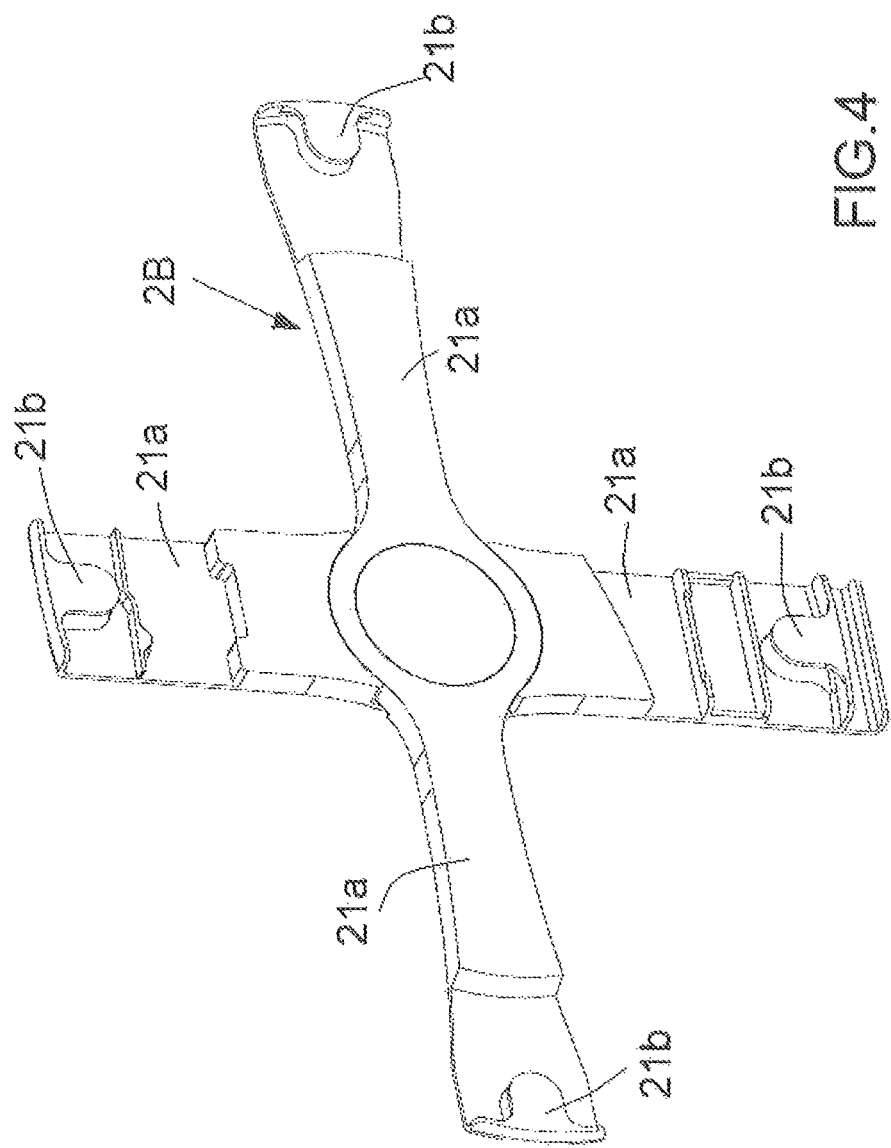
FIG. 4 is an isometric view of the storage support (without the optical fiber and without the sheath) of the assembly of FIG. 2.

In the particular embodiment variant illustrated in FIGS. 2 to 4, this storage support 2B and the positioning and guiding part 2A are separate, and can more particularly be superimposed flat on each other so as to limit their size during transport. More particularly, this storage support 2B and the positioning and guiding part 2A can in an embodiment variation be temporarily assembled, for example by clipping, and be easily separable.

The assembly in FIG. 2 is preferably packaged for its transport in an airtight packaging (not shown), for example a sachet or a blister packaging of the "blister" type, after having been previously sterilized. This assembly in FIG. 2 is removed from its packaging by the practitioner in the sterile operating field, before proceeding to the endovenous treatment.

This assembly in FIG. 2 may advantageously, but not necessarily be disposable and single use.

In the particular embodiment variant illustrated in the figures, the storage support 2B forms (FIG. 4) a rigid part in the shape of a cross with four branches 21a and is for example a single part of plastic. The sheath 3 and the optical fiber 1 are wound on this cross (FIG. 2), being inserted and blocked between elastic clips 21b at each end of the arms 21a of the cross. Once the storage support 2B is separated from the positioning and guiding part 2A (FIG. 3), the sheath 3 and the portion of the optical fiber 1 wound on this storage support 2B can be easily removed manually from the storage support 2B by an operator and be unrolled for their use.

In the context of the invention, any other form and/or any type of material for making this part having the function of a storage support 2B can be envisaged.

In addition, in the context of the invention, this storage support 2B is optional, the endovenous assembly possibly comprising only the positioning and guidance part 2A and the wire element 1 for delivering treatment doses, threaded where appropriate on a flexible guide 3.

In the particular embodiment variant in the appended figures, the positioning and guiding part 2A is a rigid one-piece flat part, for example a plastic molded part. Any other form and/or any other material for making this positioning and guiding part 2A can be envisaged.

The positioning and guiding part 2A is not necessarily one-piece and may in another variant be constituted by a rigid and monolithic assembly of several elements between them.

Figure 8:
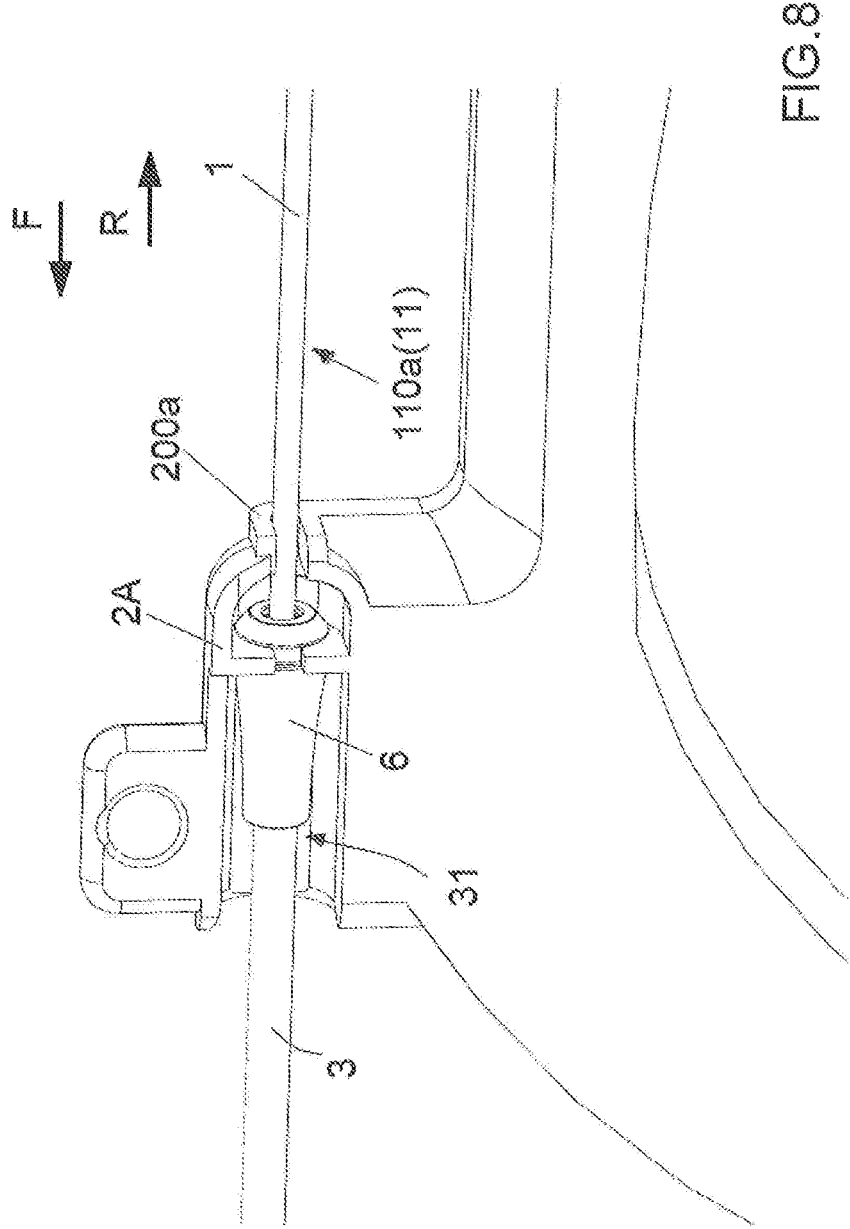
FIG. 8 is a detail view showing the attachment of the rear part of the sheath to the positioning and guiding part.

The sheath 3 has at its rear end 31 a connector 6 (FIG. 8) which is adapted to be fitted onto the positioning and guiding part 2A, so as to make the rear end 31 of the sheath 3 integral with the positioning and guiding part 2A, by obtaining an axial blocking of the rear part of the sheath 3 at least in the first direction of withdrawal R towards the rear of the wire element 1 for delivering treatment doses, and preferably also in the direction F (forward) opposite the direction of withdrawal R of the optical fiber 1. This connector 6 can also, but not necessarily, be permanently attached to the part 2A, for example by bonding.

The rear portion 11 of the optical fiber 1 which protrudes from the rear end of the sheath 3 is integral with the positioning and guiding part 2a, so as to allow the manipulation of the optical fiber 1 by means of this positioning and guiding part 2A, and the optical fiber 1 can slide in the direction of its length relative to said positioning and guiding part 2A, being partly guided by this part 2A, as will now be detailed.

More particularly, with particular reference to FIG. 2, the rear portion 11 of the optical fiber 1 comprises a first portion 110a of optical fiber 1, which extends towards the rear of the optical fiber 1 from the rear end of sheath 3 provided with connector 6, and which is preferably rectilinear.

The positioning and guiding part 2A comprises first guiding means in the form of three guiding elements 200a, 200b 200c, which are aligned and in which this first portion 110a of optical fiber 1 is threaded. These guiding elements 200a, 200b, 200c make it possible to secure the optical fiber 1 to the part 2A by guiding in translation the optical fiber 1 in this first rectilinear portion 110a, during the sliding of the optical fiber 1 in the direction of its length by compared to the part 2A.

In another variant, the positioning and guiding part 2A may comprise only one guiding element 200a, 200b or 200c or two spaced guide elements or more than three spaced guide elements.

This first portion 110a of optical fiber 1 is preferably accessible so as to allow its positioning so as to be able to be engaged with the drive means of the drive system 4, that is to say in the particular variant illustrated in the figures so as to allow its positioning between the rollers or drive rollers 40, 41.

Usually, the drive system is equipped with means for clutching/disengaging the drive rollers or rollers 40, 41. When the part 2A is mounted on the drive system, the drive rollers or rollers 40, 41 are disengaged so that they are free to rotate; the first portion 110a of optical fiber 1 is positioned between the rollers or drive rollers 40, 41, without being in engagement with its rollers or drive rollers 40, 41, which makes it possible to slide the optical fiber by hand. Then, the operator engages at least one of the two rollers or drive rollers 40, 41 for its motorized drive, so that the first portion 110a of optical fiber 1 is engaged with the rollers or rollers of drive 40, 41 and can be frictionally driven by the drive rollers or rollers 40, 41, In another variant, the drive system can be equipped in the usual way with a means of adjusting the center distance between the rollers or drive rollers 40, 41, which allows an operator to move the rollers or drive rollers 40, 41 between a separated position and a close position in which they are able to be engaged with the optical fiber 1 and to drive it by friction. When mounting the part 2A on the drive system, the rollers or drive rollers 40, 41 are in the separated position and the first portion 110a of optical fiber 1 is positioned between the rollers or drive rollers 40, 41, without being engaged with its rollers or drive rollers 40, 41, which makes it possible to be able to slide the optical fiber by hand. Then, the operator controls the approximation of the rollers or drive rollers 40, 41, so that the first portion 110a of optical fiber 1 is engaged with the rollers or drive rollers 40, 41 and can be driven by friction by the rollers or drive rollers 40, 41, In another variant, this first portion 110a of optical fiber 1 could be temporarily protected by a protection means, which can be separated from the positioning and guiding part 2A or which can be movable relative to the positioning and guiding part 2A so as to make this first portion 110a of optical fiber 1 accessible before mounting the positioning and guiding part 2A relative to the drive means of the drive system 4 or once the positioning and guiding part 2A mounted relative to the drive means of the drive system 4.

In this variant, the first portion 110a of optical fiber 1 is extended towards the rear by a second portion 110b (FIG. 6), and the part 2A comprises second guide means 201, which make it possible to secure the optical fiber 1 to the part 2A and to guide in translation the optical fiber 1 in this second portion 110b, during the sliding of the optical fiber 1 in the direction of its length relative to the part 2A.

More particularly, in this embodiment variant this second portion 110b is curved, the second guide means guiding in translation this second portion 110b of the optical fiber 1 by advantageously making it perform a half turn.

Figure 6:
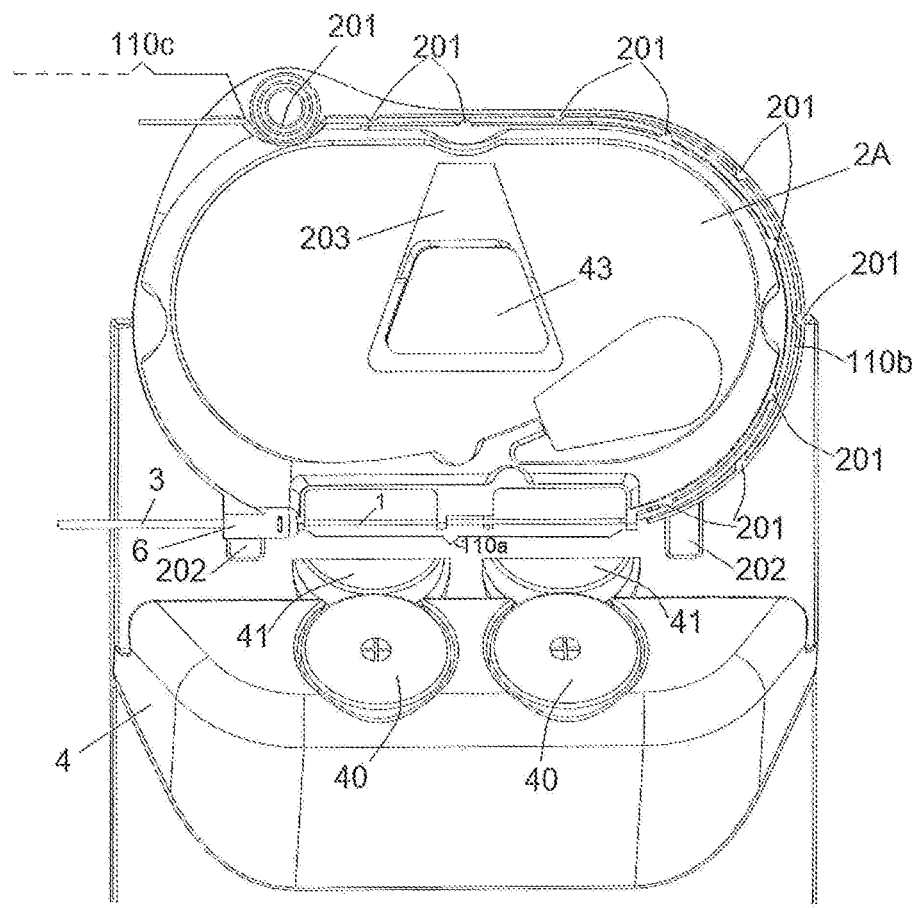
FIG. 6 is an isometric view of the assembly of FIG. 3 during assembly of the positioning and guiding part on the drive system of FIG. 5.
Figure 7:
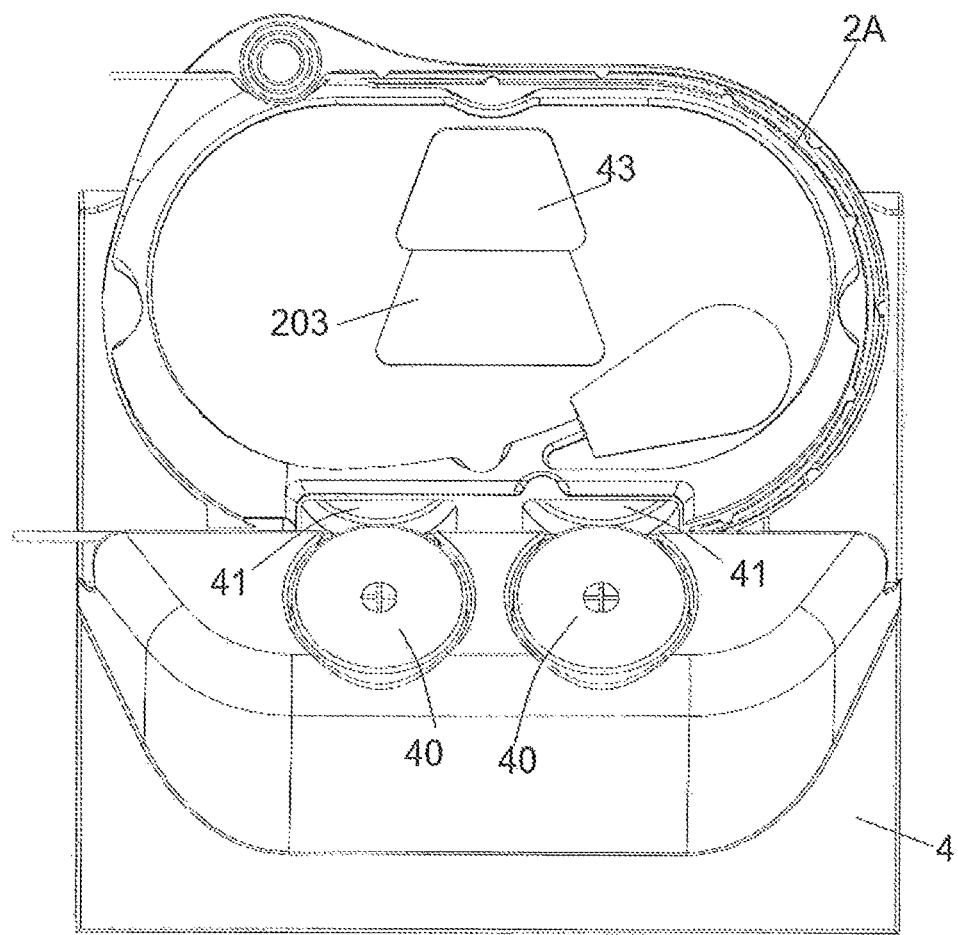
FIG. 7 is an isometric view of the assembly of FIG. 3, once the positioning and guiding part is mounted on the drive system.

The second portion 110b of optical fiber 1 extends to the rear end 1a of the optical fiber 1 by a third portion 110c (FIGS. 2 and 6). At this rear end of the optical fiber 1 is attached an optical coupler 112 for coupling the optical fiber to the laser source L. In this embodiment variant, this third portion 110c of the optical fiber 1 and the optical coupler 112 are integral temporarily with part 2A, being nested in part 2A and can be easily removed manually from part 2A by an operator (FIG. 3) and unrolled in order to couple the optical fiber 1 to the laser source L.

In another embodiment variant, this third portion 110c of the optical fiber 1 and the optical coupler 112 can be separated from the part 2A all the time.

Figure 5:
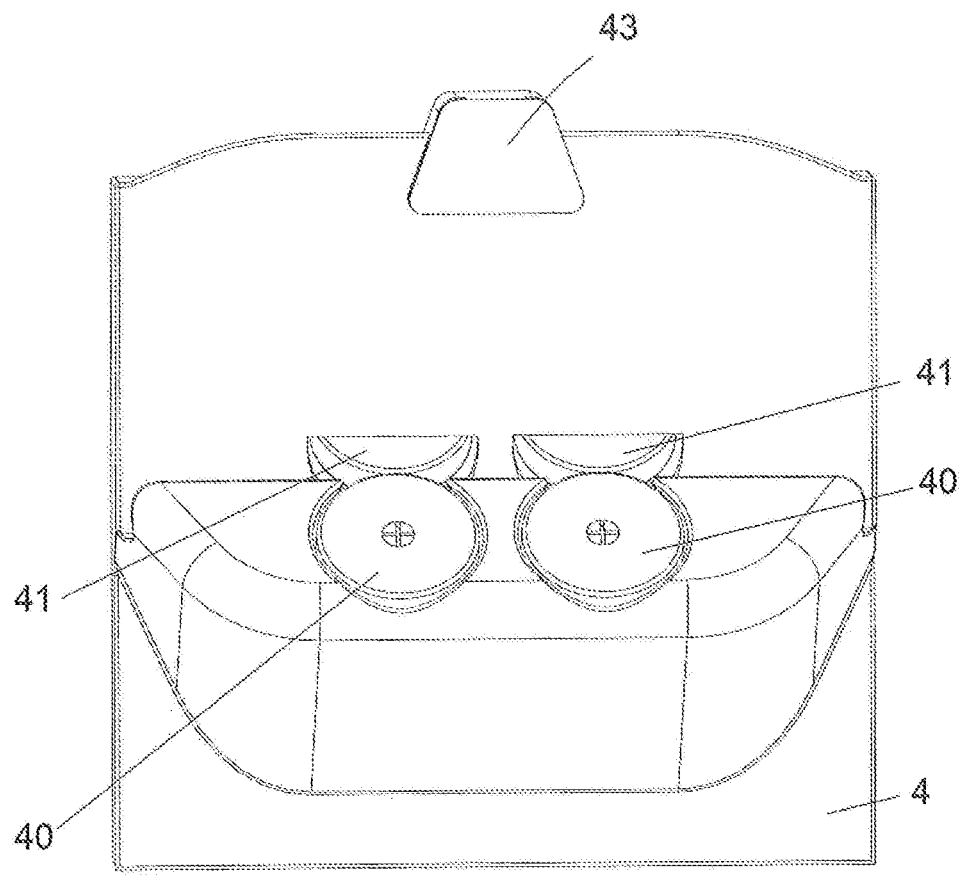
FIG. 5 represents an example of a drive system.
Figure 9:
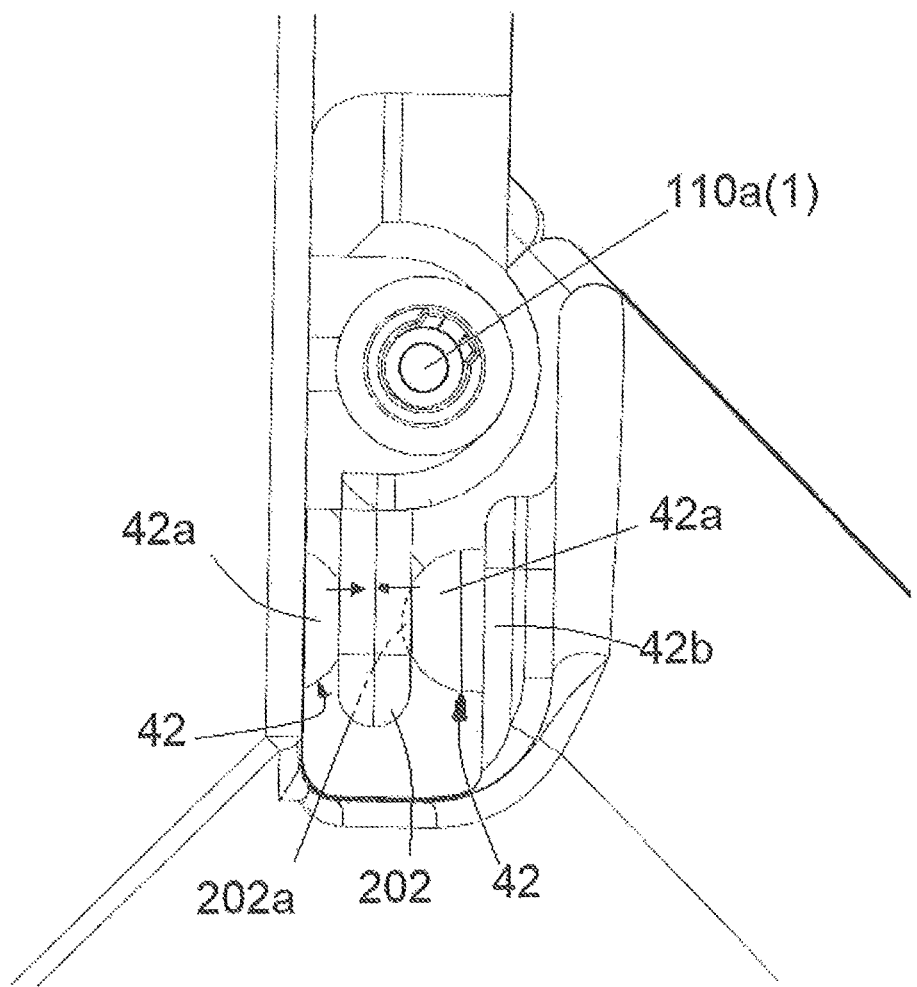
FIG. 9 is a cross-sectional view showing the indexing of the assembly tabs of the positioning and guiding part with respect to the drive system.

With reference to FIG. 2, the positioning and guiding part 2A comprises first mechanical assembly means 202, 203 able to cooperate with second mechanical assembly means 42, 43, which in this variant form an integral part of the drive system 4 (FIGS. 5 and 9). These first 202, 203 and second 42, 43 mechanical assembly means allow removable, rapid and tool-free mounting of the positioning and guiding part 2A relative to the drive system 4, and more particularly in this variant removable, quick and tool-free mounting of part 2A on the drive system 4.

Once the positioning and guiding part 2A is mounted relative to the drive system 4, said first portion 110a of the optical fiber 1 is positioned between the drive rollers 40, 41 of the drive system 4 for the rear friction drive (arrow R) of the optical fiber 1 by the drive rollers 40, 41.

In this particular embodiment variant and without limitation of the invention, with reference to FIGS. 2 and 9, the first mechanical assembly means comprise a recess 203 in the part 2A and two assembly tabs 202 which form an integral part of part 2A and which comprise at least on one face a hemispherical housing 202a (FIG. 9). With reference to FIGS. 5, 6, 7 and 9, in this variant the second mechanical assembly means form an integral part of the drive system 4 and comprise a hooking element 43, which is adapted to cooperate with the recess 203 in part 2A and two indexing elements 42 for each assembly tab 202 (FIG. 9), which are positioned on either side of the assembly tab 202, when part 2A is mounted on the drive system 4.

With reference to FIG. 9, each indexing element 42 comprises a ball 42*a* which is pushed elastically in the direction of the assembly tab 202 in the locking position in FIG. 9, by a spring (not visible) housed in a cylindrical body 42*b*. When the part 2A is mounted on the drive system 4, one of the two balls 42*a* (right ball in FIG. 9) is resiliently pushed back so as to be housed partly in the hemispherical housing 202*a* of the assembly tab 202 and the other ball 42*a* (left ball in FIG. 9) is pushed elastically so as to come into abutment against the assembly tab 202.

Initially, with reference to FIG. 2, the largest portion of the optical fiber 1 surrounded by the sheath 3 is conditioned by being wound on the storage support 2B. The connector 6 at the rear end 31 of the sheath 3 is integral with the positioning and guiding part 2A, as previously described. The rear part 11 of the optical fiber 1 devoid of sheath 3 is integral with the positioning and guiding part 2A, as previously described; the storage support 2B is superimposed with the positioning and guiding part 2A. The assembly is thus compact, and can be easily handled and/or stored and/or transported.

To position the optical fiber 1 of this assembly relative to the drive system 4, the procedure is as follows.

If necessary, separate the storage support 2B and the positioning and guiding part 2A.

The third portion 110*c* of the optical fiber is removed from the positioning and guiding part 2A, carrying the optical coupler 112 at its end (FIG. 3).

The positioning and guiding part 2A is mounted with the optical fiber 1 on the drive system 4, which makes it possible to position easily, quickly and precisely, the first straight portion 110*a* of the optical fiber between the drive rollers 40, 41.

In this particular variant, this assembly is carried out in two phases. In a first phase (FIG. 6), the part 2A is positioned relative to the drive system 4, by vertically and horizontally aligning the recess 203 of the part 2A relative to the hooking element 43, as illustrated in FIG. 6. In a second phase (FIG. 7), the part 2A is lowered vertically relative to the drive system 4, so as to insert the upper edge of the recess 203 in the hooking element 43.

During this downward movement, the assembly tabs 202 are positioned between their indexing elements 42. This lowering of the part 2A is carried out as far as the indexing position in FIG. 9.

This removable mounting of the part 2A allows an operator to quickly and reliably position the first portion 110*a* of the optical fiber 1 between the drive rollers 40, 41. When these rollers 40, 42 drive the optical fiber 1 by pulling on this first portion 110*a*, the optical fiber 1 slides with respect to the sheath 3 while being guided by the guiding means 200*a*, 200*b*, 200*c* and 201 of the part 2A.

Once the part 2A has been assembled, the front part 30 of the sheath 3 can be fixed to the retaining part 50 of the holding system 5 (FIG. 10) and the device is then ready to be used for making an endovenous treatment, for example and without limitation of the invention in the following manner.

Figure 10:
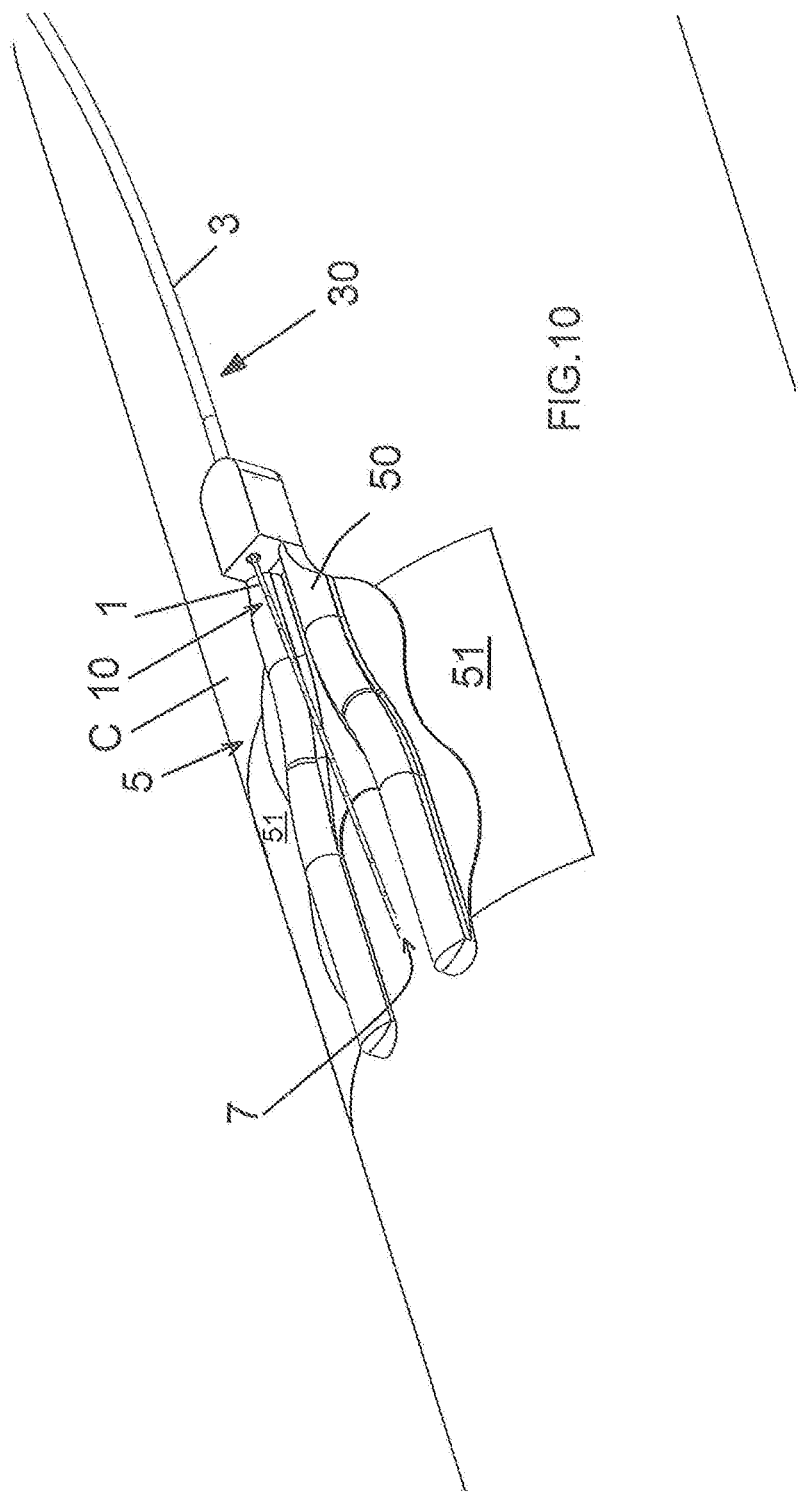
FIG. 10 is an isometric view of an example of a sheath holding system placed on and attached to a part of a human body, with the optical fiber inserted through the skin.
Figure 11:
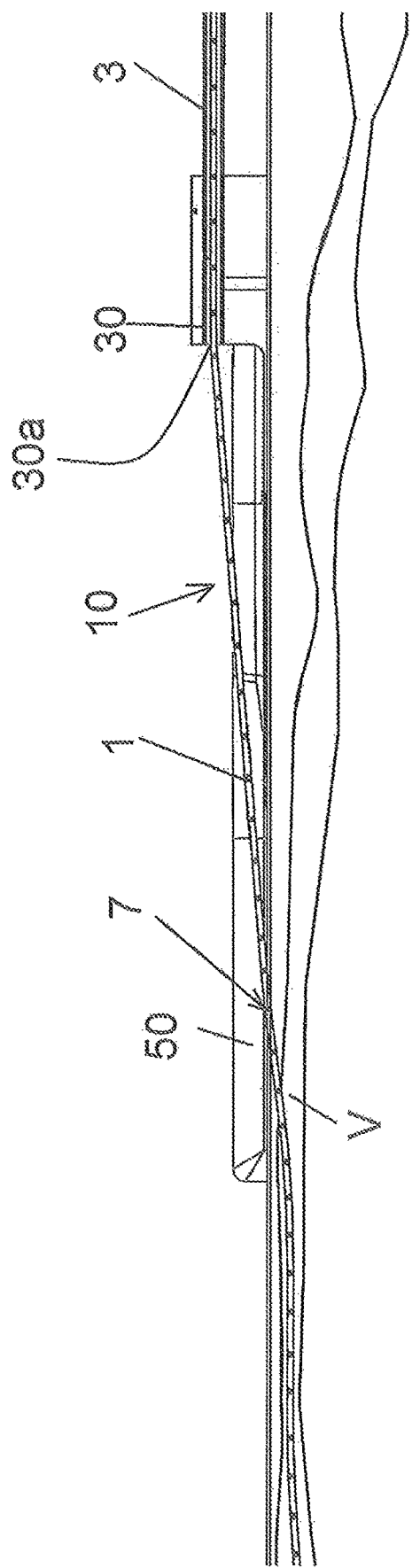
FIG. 11 is a longitudinal sectional view of FIG. 10, showing in particular the vein and the optical fiber inserted into the vein.

(a) The front end part 30 of the sheath is attached relative to the body C, by fixing the holding part 50 to the human body C near the insertion point 7 of the optical fiber 1, for example using an adhesive 51 (FIG. 10).

(b) A hollow needle, commonly known as a puncture needle, whose tip is ultrasonically localized by means of an ultrasound probe, is routinely pushed through the skin and into the vein V to be treated. The insertion point of this needle corresponds to the insertion point 7 referred to above.

(c) A guidewire is inserted into this hollow needle into the vein to be treated, and then the needle is removed.

Figure 12:
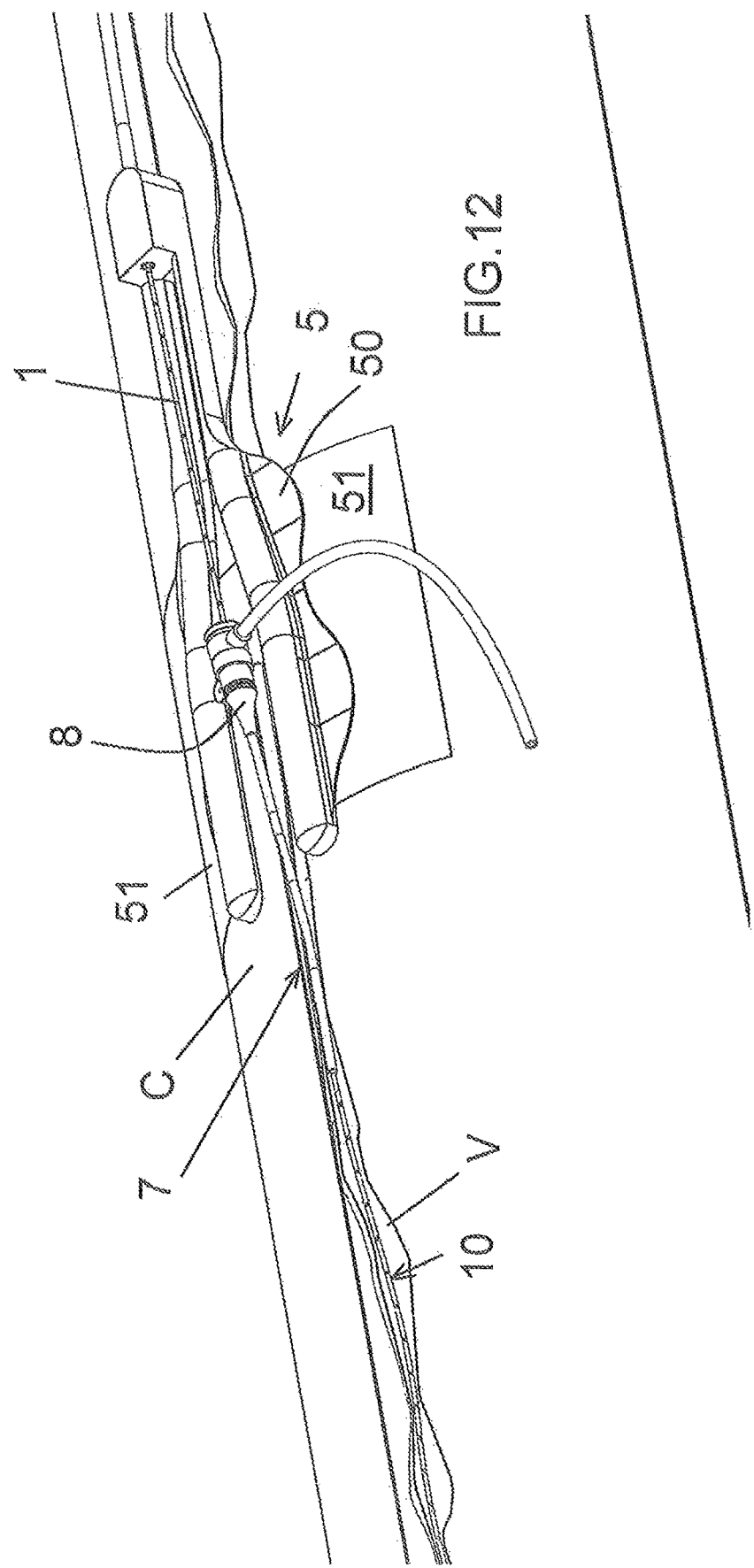
FIG. 12 is an isometric view illustrating a stage in the insertion of the extreme front end portion of the optical fiber into a vein, by means of an introducer catheter.

(d) An introducer catheter 8 is threaded onto the guide wire up to the entrance of the vein V and the guide wire is removed (FIG. 12).

(e) Once the introducer catheter 8 has been inserted (FIG. 12), the front end part 10 of the optical fiber 1, which protrudes outside the front end part 30 of the sheath 3, is inserted into the introducer catheter 8 and the optical fiber 1 is slid forwardly relative to the sheath 3 until the end of the front end part 10 of optical fiber 1 penetrates longitudinally into the vein V and progresses into vein V to the area to be treated furthest from the insertion point 7. During this operation, the drive motor of the rollers of the drive system 4 is disengaged.

Figure 13:
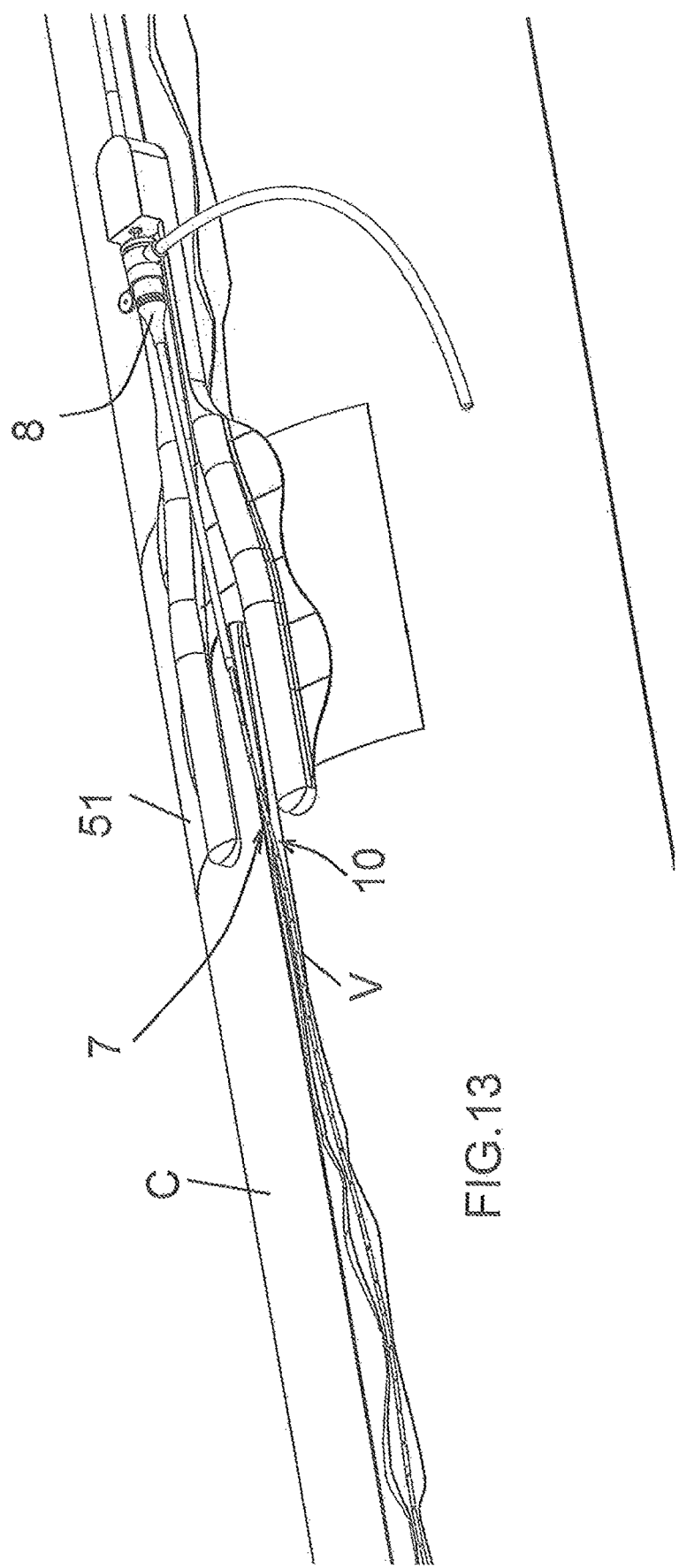
FIG. 13 is an isometric view showing the introducer catheter of FIG. 12 removed from the vein once the extreme front end portion of the optical fiber has been introduced into a vein.

(f) Once the optical fiber 1 is introduced and positioned into the vein V, the catheter 8 is withdrawn from the vein V by sliding it backwards along the optical fiber 1 (FIG. 13). Optionally, the catheter 8 is removed from the optical fiber 1, for example by splitting it in two in the case of a tearable catheter. In another variant, the catheter may be removed following completion of the treatment procedure.

The practitioner can then conduct the endovenous treatment by manually operating the laser source L, in order to emit electromagnetic radiation into the vein in the region of the end of the proximal part of the optical fiber 1 and by controlling the withdrawal, either continuous or step by step, of the optical fiber 1 by means of the withdrawal system 4.

Thanks to the guide sheath 3, whose front end part 30 is temporarily attached to the body C, near the insertion point 7 of the optical fiber 1, and whose rear end part 31 is locked axially relative to the optical fiber 1 by means of the connector 6, the endovenous treatment can advantageously be performed without the optical fiber 1 being tensioned and reducing the risk of accidental movement of the optical fiber relative to the vein being treated.

Once the laser treatment is complete, the optical fiber 1 is completely removed from the vein and the holding system 5 is separated from the human body. The practitioner can then disconnect the optical fiber 1 from the laser source L, and remove the part 2A with the optical fiber 1 from the drive system 4.

In the embodiment variant in FIG. 1, the rear part 11 of the optical fiber 1 is advantageously guided and returned towards the front by the second guide means 201 of the part 2A, thanks to the half turn carried out by the second rear portion 110*b* of the fiber 1. Thus, when the optical fiber 1 is withdrawn towards the rear (arrow R), the optical fiber 1 being maintained and guided by the second guide means 201, the risk of accidental catching in the optical fiber by a person or an object is avoided.

More generally, the second guide means 201 can be designed to guide in translation this second portion 110*b* of the wire element 1 for delivering treatment doses by making it perform at least a quarter turn.

In another embodiment variant, the second portion 101*b* of the optical fiber 1 which is guided so as to perform at least a quarter turn is not necessarily located in the rear extension of the first portion 101*a* of the optical fiber 1, but can be positioned in the front extension of the first portion 101*a* of the optical fiber 1. In addition, the second guide means 202 are not necessarily an integral part of the part 2A, but could be separate and separate guide means from this part 2A.

Preferably, the second mechanical assembly means 42, 43 are integral with or form an integral part of the drive system 4. However, in another embodiment variant, the second mechanical assembly means 42, 43 can be separated from the drive system 4 and can for example be attached to or form an integral part of a table-type support, on which the drive system 4 would be placed.

The invention is not limited to an endovenous laser treatment device. In other variants covered by the invention, the optical fiber may be replaced by a wire element (solid or hollow) for example of the cable or flexible probe or flexible cannula type. The treatment may not necessarily be a laser treatment, but may be any treatment consisting of the delivery of doses of treatment into the vein, and especially of doses of energy, delivered for example in the form of electromagnetic radiation, by means of sound or ultrasonic waves, radiofrequency waves, or doses of thermal energy delivered by radiation and/or by contact, or doses of a product, for example liquid, semi-liquid or foam, allowing treatment of the vein.

The removal system 4 can in a more general manner be replaced by any drive system allowing the treatment dose delivery wire element 1 to be drawn in at least one given drive direction R. This drive system 4 of the device is not necessarily motorized, but could be a manually operated drive system.

In the context of the invention, the guide sheath 3 can be replaced by any equivalent flexible guide that fulfills the same guiding function as the sheath 3. For example, and non-exhaustively, the sheath 3 may be replaced by a flexible groove-shaped guide, having for example a U-shaped cross section, or by a flexible wire guide twisted around the optical fiber 1 or equivalent, or by a flexible guide which is magnetized to allow it to be secured to the wire element 1 for delivery of the treatment doses.

The flexible guide 3 is not necessarily made in one piece but may include several assembled elements. For example, the guide 3 may comprise a flexible guide sheath or equivalent at the front end of which a rigid introducer catheter would be attached, the holding system 5 making it possible to temporarily hold this introducer catheter on the patient's body.

The holding system 5 may comprise only the holding part 50 or equivalent and may not include the fastening means 51 or equivalent. In this case, the holding part 50 is used to temporarily hold the proximal end part 30 of the guide 3 manually relative to the patient's body near the insertion point 7 of the wired treatment dose delivery element 1. This temporary holding of the proximal end part 30 of the guide 3 relative to the patient's body near the insertion point 7 of the wire element 1 for delivering treatment doses can be done by positioning the holding part 50 or equivalent in contact with the patient or by holding the holding part 50 or equivalent in the hand and by applying in contact with the patient the hand holding this holding part 50 or equivalent.

The holding system may comprise an attachment facility for temporarily attaching the proximal end part 30 of the guide 3 on the body of a patient, near the insertion zone 7 of the wired treatment dose delivery element 1, without use of the holding part 50. For example, the holding system may be formed of one or more adhesives capable of being applied directly to the front end part 30 of the guide 3 and to be adhered to the patient's body to temporarily attach the front end part 30 of the guide 3 relative to the body of the patient near the insertion point 7 of the wired treatment dose delivery element 1.

The invention claimed is:

1. An endovenous treatment assembly comprising:
a wire element for delivering treatment doses, which is flexible and capable of being inserted, over a portion of its length, longitudinally into a vein;
a positioning and guiding part that is integral with and manipulates the wire element, said positioning and guiding part comprising:
at least a first guiding element for guiding in translation the wire element in a first portion of the wire element and in the direction of its length, where the wire element is able to slide in the direction of its length relative to the entire at least first guiding element; and,
a first mechanical assembly allowing for removable mounting of the positioning and guiding part relative to a driver of a drive system, so that said first portion of the wire element for delivering treatment doses can be positioned and guided by the positioning and guiding part and can be engaged in direct contact with the drive system for driving the wire element in the direction of its length in at least in a first direction.

2. The endovenous treatment assembly according to claim 1, wherein said first portion of the wire element for delivering treatment doses is accessible or can be made accessible.

3. The endovenous treatment assembly according to claim 1 wherein said first portion of the wire element is positioned and guided by the positioning and guiding part so as to be able to be engaged with the drive system for driving the wire element in the direction of its length at least in the first direction, with a displacement of the wire element in the direction of its length relative to said drive system.

4. The endovenous treatment assembly according to claim 1 further comprising a second guide of a second portion of the wire element.

5. The endovenous treatment assembly according to claim 4, in which the second guide guides in translation the second portion of the wire element for delivering treatment doses by making it perform between at least a quarter turn and at least half a turn.

6. The endovenous treatment assembly according to claim 4 wherein the second guide forms an integral part of the positioning and guiding part.

7. The endovenous treatment assembly according to claim 4 wherein the wire element for delivering treatment doses further comprises a third portion, which extends to the rear end of the wire element, and which is not integral with the positioning and guiding part or which is integral with the positioning and guiding part but can be separated from the positioning and guiding part.

8. The endovenous treatment assembly according to claim 1 further comprising a coupler which is attached to a rear end of the wire element and which makes it possible to connect the wire element to a treatment dose source.

9. The endovenous treatment assembly according to claim 1 wherein the positioning and guiding part is one of a single part, a molded part, or is constituted by a monolithic assembly.

10. The endovenous treatment assembly according to claim 1 further comprising a flexible guide threaded on a front portion of the wire element, said wire element being able to slide longitudinally with respect to the flexible guide.

11. The endovenous treatment assembly according to claim 10, wherein a rear end of the flexible guide is integral with the positioning and guiding part, so as to axially block the rear end part of the flexible guide in at least one of in the first drive direction of the wire element, and also in the direction opposite to the drive direction of the wire element.

12. The endovenous treatment assembly according to claim 11 further comprising a storage support on which is wound all or part of a front portion of the wire element which extends from a front end of the wire element to said first portion of the wire element for delivering treatment doses.

13. The endovenous treatment assembly according to claim 12 wherein the flexible guide and a portion of the wire element is threaded into the flexible guide and is wound on the storage support.

14. The endovenous treatment assembly according to claim 12 wherein the storage support and the positioning and guiding part are separated or in which the storage support and the positioning and guiding part are assembled and separable from each other.

15. The endovenous treatment assembly according to claim 12 wherein the positioning and guiding part, the wire element, the flexible guide, and the storage support, are sterile and placed in an airtight package.

16. The endovenous treatment assembly according to claim 1 wherein the wire element is an optical fiber.

17. The endovenous treatment assembly according claim 1 wherein the first mechanical assembly allows rapid and tool-free assembly of the positioning and guiding part.

18. The endovenous treatment assembly according to claim 1, wherein the first mechanical assembly is adapted for the removable mounting of the positioning and guiding part relative to the drive system which comprises at least one pair of drive rollers, so that said first portion of the wire element for delivering treatment doses can be positioned and guided by the positioning and guiding part between the drive rollers for driving the wire element for delivery of treatment doses in the direction of its length at least in the first direction.

19. An endovenous treatment device comprising:
an assembly comprising:
a wire element for delivering treatment doses, which is flexible and capable of being inserted, over a portion of its length, longitudinally into a vein;
a positioning and guiding part that is integral with and manipulates the wire element, said positioning and guiding part comprising:
at least a first guiding element for guiding in translation the wire element in a first portion of the wire element and in the direction of its length, where the wire element is able to slide in the direction of its length relative to the entire at least first guiding element; and,
a first mechanical assembly allowing for removable mounting of the positioning and guiding part relative to a driver of a drive system, so that said first portion of the wire element for delivering treatment doses can be positioned and guided by the positioning and guiding part and can be engaged in direct contact with the drive system for driving the wire element in the direction of its length in at least in a first direction;
the drive system, where said driver of said drive system comprises rotary drive rollers; and
a second mechanical assembly adapted to cooperate with the first mechanical assembly of the positioning and guiding part, so as to allow removable mounting of the positioning and guiding part relative to the drive system, so that said first portion of the wire element is positioned so as to be able to be engaged with the rotary drive rollers of the drive system and the rotary drive rollers allow the drive of the wire element to deliver treatment doses in the direction of the wire element length at least in a first direction, with a displacement of the wire element for delivering the treatment doses in the direction of its length relative to said rotary drive rollers.

20. The endovenous treatment device according to claim 19, wherein the second mechanical assembly is integral with or forms an integral part of the drive system.

21. The endovenous treatment device according to claim 19, in which the drive system and the second mechanical assembly are adapted to cooperate with the first mechanical assembly of the positioning and guiding part, so as to allow the positioning of the first portion of the wire element for delivering treatment doses between the drive rollers.

22. The endovenous treatment device according to claim 19 wherein the rotary drive rollers provide friction drive of the wire element for delivering treatment doses.

23. The endovenous treatment device according to claim 19 further comprising a source of treatment doses able to be connected to a rear end of the wire element for delivering treatment doses.

24. The endovenous treatment device according to claim 23, in which the drive system and the treatment dose source are an integral part of a monolithic assembly.

25. The endovenous treatment device according to claim 23 wherein the wire element is an optical fiber and the treatment dose source is a source of electromagnetic radiation.

26. A method comprising:
providing an endovenous treatment device, the device comprising:
an assembly comprising:
a wire element for delivering treatment doses, which is flexible and capable of being inserted, over a portion of its length, longitudinally into a vein;
a positioning and guiding part that is integral with and manipulates the wire element, said positioning and guiding part comprising:
at least a first guiding element for guiding in translation the wire element in a first portion of the wire element and in the direction of its length, where the wire element is able to slide in the direction of its length relative to the entire at least first guiding element; and,
a first mechanical assembly allowing for removable mounting of the positioning and guiding part relative to a driver of a drive system, so that said first portion of the wire element for delivering treatment doses can be positioned and guided by the positioning and guiding part and can be engaged in direct contact with the drive system for driving the wire element in the direction of its length in at least in a first direction,
where said driver of said drive system comprises rotary drive rollers; and
wherein the device further comprises:
a second mechanical assembly adapted to cooperate with the first mechanical assembly of the positioning and guiding part, so as to allow removable mounting of the positioning and guiding part relative to the drive system, so that said first portion of the wire element is positioned so as to be able to be engaged with the rotary drive rollers of the drive system and the rotary drive rollers allow the drive of the wire element to deliver treatment doses in the direction of the wire element length at least in a first direction, with a displacement of the wire element for delivering the treatment doses in the direction of its length relative to said rotary drive rollers, and removably mounting the positioning and guiding part relative to the drive system so that the first portion of the wire element is positioned so as to be able to be engaged with the rotary drive rollers and can be driven at least in the first drive direction.

\* \* \* \* \*